US006277851B1

United States Patent
De Nanteuil et al.

(10) Patent No.: US 6,277,851 B1
(45) Date of Patent: Aug. 21, 2001

(54) BICYCLIC AMINO-PYRAZINONE COMPOUNDS

(75) Inventors: Guillaume De Nanteuil, Suresnes; Philippe Gloanec, Bougival; Tony Verbeuren, Vernouillet; Alain Rupin, Savonnieres; Marie-Odile Vallez, Champs sur Marne, all of (FR)

(73) Assignee: Adir et Compagnie, Courbevoie (FR)

(*) Notice: Subject to any disclaimer, the term of this patent is extended or adjusted under 35 U.S.C. 154(b) by 0 days.

(21) Appl. No.: 09/594,852

(22) Filed: Jun. 15, 2000

(30) Foreign Application Priority Data

Jun. 15, 1999  (FR) .................................................. 9907538

(51) Int. Cl.[7] ........................ A61K 31/50; A61K 31/495; C07D 471/00; C07D 487/00
(52) U.S. Cl. .......................... 514/249; 544/349; 544/350
(58) Field of Search .................... 544/349, 350; 514/249

(56) References Cited

FOREIGN PATENT DOCUMENTS

93/08188 * 4/1993 (WO) .

* cited by examiner

Primary Examiner—Mukund J. Shah
Assistant Examiner—Tamthom N. Truong
(74) Attorney, Agent, or Firm—The Firm of Hueschen and Sage; G. Patrick Sage

(57) ABSTRACT

A compound selected from those of formula (I):

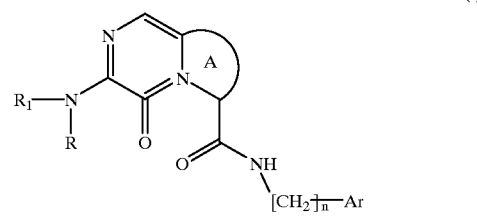

wherein:
  $R_1$ represents hydrogen, optionally substituted alkyl, cycloalkyl or heterocycloalkyl or a group of formula (G):

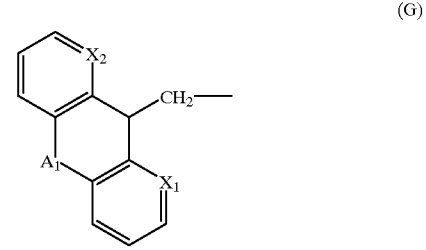

wherein $A_1$ represents single, —$CH_2$—, —$CH_2$—$CH_2$— or —$N(CH_3)$— or oxygen or sulphur, and $X_1$ and $X_2$, which may be identical or different, each represent carbon or nitrogen,
  R represents hydrogen or linear or branched ($C_1$–$C_6$) alkyl,

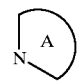

represents a saturated ring having from 4 to 7 ring members,
  n represents integer wherein $1 \leq n \leq 6$,
  Ar represents aryl or heteroaryl,
its isomers, N-oxydes and pharmaceutically-acceptable acid or base addition salts thereof.

8 Claims, No Drawings

BICYCLIC AMINO-PYRAZINONE COMPOUNDS

FIELD OF THE INVENTION

The present invention relates to new bicyclic amino-pyrazinone compounds, to pharmaceutical compositions containing them, and to their use as inhibitors of trypsin-related serine proteases.

One of those serine proteases, thrombin, is the key enzyme for coagulation and plays a central role in the pathology of venous and arterial thromboses, especially in view of its marked ability to cause auto-amplification of the coagulation cascade (F. Toti et al., Sang, Thrombose, Vaisseaux [Blood, Thrombosis, Vessels] 1992, 4, 483–494 and T. M. Reilly et al., Blood Coagulation and Fibrinolysis 1992, 3, 513–517).

The direct and specific inhibition of thrombin is more efficient and poses fewer risks of haemorrage than treatment with heparin. Direct inhibitors of thrombin currently exist but the disadvantage of those peptide substances is that they are not active when administered by the oral route.

Peptidomimetic compounds having an oral antithrombotic activity have already been described in the literature. They include, for example, the boronic acid compounds described in Patent Specifications EP 293 881, EP 471 651, EP 615 978 and EP 792 883 and the compounds described in Patent Specifications WO 94 29336 and WO 95 23609.

It has therefore been of particular interest to synthesise new serine protease inhibitors in order to increase the effectiveness and selectivity of compounds already described in the literature.

The activity of those new compounds is demonstrated by the increase in various coagulation times.

The compounds are, moreover, active when administered by the oral route.

DETAILED DESCRIPTION OF THE INVENTION

More specifically, the present invention relates to compounds of formula (I):

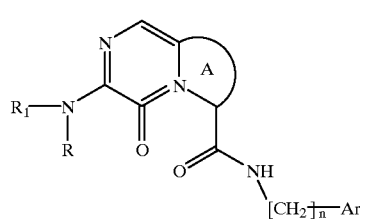

(I)

wherein:

$R_1$ represents a hydrogen atom or a linear or branched ($C_1$–$C_6$)alkyl group (optionally substituted by one or more identical or different substituents selected from aryl, heteroaryl, cycloalkyl, heterocycloalkyl, carboxy, linear or branched ($C_1$–$C_6$)-alkoxycarbonyl, and carbamoyl groups), a hydroxy group, a cycloalkyl group, a heterocycloalkyl group or a group of formula (G):

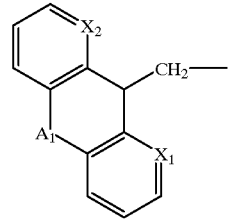

(G)

wherein $A_1$ represents a single bond, a —$CH_2$—, —$CH_2$—$CH_2$— or —$N(CH_3)$— group or an oxygen or sulphur atom, and $X_1$ and $X_2$, which may be identical or different, each represent a carbon or nitrogen atom, R represents a hydrogen atom or a linear or branched ($C_1$–$C_6$)alkyl group,

represents a saturated ring having from 4 to 7 ring members that may contain in addition to the nitrogen atom one or two hetero atoms selected from O and S, or —$N(R_2)$— groups, $R_2$ represents a hydrogen atom or a linear or branched ($C_1$–$C_6$)alkyl group, n represents an integer wherein $1 \leq n \leq 6$, Ar represents an aryl or heteroaryl group, its isomers, N-oxydes and pharmaceutically-acceptable acid or base addition salts thereof.

Among the pharmaceutically acceptable acids there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid, camphoric acid, etc..

Among the pharmaceutically acceptable bases there may be mentioned by way of non-limiting example sodium hydroxide, potassium hydroxide, triethylamine, tert-butylamine, etc.

"Aryl group" is understood to mean phenyl, biphenylyl or naphthyl, each of those groups being optionally substituted by one or more halogen atoms and/or by one or more identical or different groups selected from linear or branched ($C_1$–$C_6$)alkyl (optionally substituted by a hydroxy or carboxy group or by a carbamoyl group (itself optionally substituted by one or two linear or branched ($C_1$–$C_6$)alkyl groups)), linear or branched ($C_1$–$C_6$)alkoxy, hydroxy, trihalo-($C_1$–$C_6$)alkyl in which the alkyl moiety is linear or branched, trihalogenoalkoxy in which the alkyl moiety is linear or branched, amino (optionally substituted by one or two linear or branched ($C_1$–$C_6$)alkyl groups), linear or branched alkylcarbonyloxy group, carboxymethoxy and carbamoylmethoxy (optionally N-substituted by one or two linear or branched ($C_1$–$C_6$)alkyl groups).

"Heteroaryl group" is understood to mean a mono- or bi-cyclic aromatic group having from 5 to 12 ring members and containing one, two or three hetero atoms selected from oxygen, nitrogen and sulphur, it being understood that the heteroaryl may be optionally substituted by one or more halogen atoms and/or by one or more identical or different groups selected from linear or branched ($C_1$–$C_6$)alkyl (optionally substituted by a hydroxy or carboxy group or by a carbamoyl group (itself optionally substituted by one or two linear or branched ($C_1$–$C_6$)alkyl groups)), hydroxy, linear or branched ($C_1$–$C_6$)alkoxy, trihalo-($C_1$–$C_6$)alkyl in which the alkyl moiety is linear or branched, phenyl, amino (optionally N-substituted by one or more linear or branched ($C_1$–$C_6$)alkyl groups), carboxymethoxy and carbamoylmethoxy (optionally substituted by one or two linear or branched ($C_1$–$C_6$)alkyl groups).

Among the heteroaryl groups there may be mentioned by way of non-limiting example the thienyl, pyridyl, furyl, pyrrolyl, imidazolyl, oxazolyl, isoxazolyl, thiazolyl, isothiazolyl, pyrimidinyl, pyrazinyl and pyridazinyl groups.

"Cycloalkyl group" is understood to mean a saturated or unsaturated mono- or bi-cyclic hydrocarbon group having from 3 to 12 ring members, it being understood that the ring system may be optionally substituted by one or more halogen atoms and/or by one or more identical or different groups selected from linear or branched ($C_1$–$C_6$)alkyl, linear or branched ($C_1$–$C_6$)alkoxy, hydroxy, trihalo-($C_1$–$C_6$)alkyl in which the alkyl moiety is linear or branched, amino (optionally substituted by one or more linear or branched ($C_1$–$C_6$)alkyl groups) and aryl.

Among the cycloalkyl groups there may be mentioned by way of non-limiting example the cyclopentyl, cyclohexyl, indanyl and tetrahydronaphthyl groups.

"Heterocycloalkyl group" is understood to mean a saturated or unsaturated, mono- or bi-cyclic group having from 4 to 12 ring members and containing one, two or three hetero atoms selected from oxygen, nitrogen and sulphur, it being understood that the heterocycle may be optionally substituted by one or more halogen atoms and/or by one or more identical or different groups selected from linear or branched ($C_1$–$C_6$)alkyl, linear or branched ($C_1$–$C_6$)alkoxy, hydroxy, trihalo-($C_1$–$C_6$)alkyl in which the alkyl moiety is linear or branched, amino (optionally substituted by one or more linear or branched ($C_1$–$C_6$)alkyl groups), aryl and diarylmethyl.

Among the heterocycloalkyl groups there may be mentioned by way of non-limiting example the azetidinyl, pyrrolidinyl, piperidyl and dihydrocyclopenta[b]pyridyl groups.

The preferred compounds of formula (I) are those wherein n is 1.

The ring

as defined for formula (I) is preferably a pyrrolidinyl group.

The group Ar as defined for formula (I) is preferably a phenyl or pyridyl group, each of those groups being optionally substituted by one or more halogen atoms and/or by one or more identical or different groups selected from linear or branched ($C_1$–$C_6$)alkyl (optionally substituted by a hydroxy or carboxy group or by a carbamoyl group (itself optionally substituted by one or two linear or branched ($C_1$–$C_6$)alkyl groups)), linear or branched ($C_1$–$C_6$)alkoxy, hydroxy, trihalo-($C_1$–$C_6$)alkyl in which the alkyl moiety is linear or branched, amino (optionally substituted by one or two linear or branched ($C_1$–$C_6$)alkyl groups), carboxymethoxy and carbamoylmethoxy (optionally N-substituted by one or two linear or branched ($C_1$–$C_6$)alkyl groups).

The invention relates also to a process for the preparation of compounds of formula (I), characterised in that a compound of formula (II):

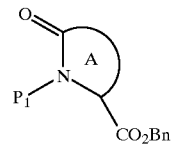

(II)

wherein A is as defined for formula (I), $P_1$ represents an amino-function-protecting group and Bn represents a benzyl group,
is reduced using an appropriate reducing agent,
to yield a compound of formula (III):

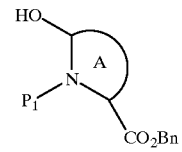

(III)

wherein A, $P_1$ and Bn are as defined hereinbefore, the hydroxy function of which compound of formula (III) is converted to the methoxy function and then to the cyano function by conventional organic chemistry reactions, to yield, after deprotection of the amino function, a compound of formula (IV):

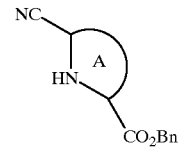

(IV)

wherein A and Bn are as defined hereinbefore,
which compound of formula (IV) is reacted with oxalyl chloride to yield a compound of formula (V):

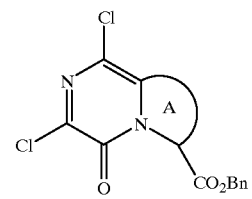

(V)

wherein A and Bn are as defined hereinbefore,
which compound of formula (V) is reacted with a compound of formula (VI):

(VI)

wherein $R_1$ is as defined for formula (I), to yield a compound of formula (VII):

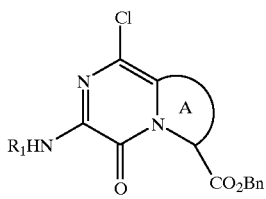
(VII)

wherein A, Bn and $R_1$ are as defined hereinbefore,
which compound of formula (VII) is then converted by catalytic hydrogenation to a compound of formula (VIII):

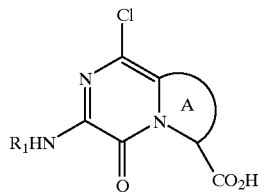
(VIII)

wherein A and $R_1$ are as defined hereinbefore,
which compound of formula (VIII) is then converted by catalytic hydrogenation in an alkaline medium to a compound of formula (IX):

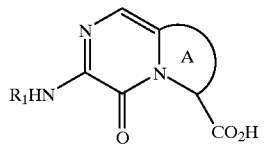
(VIII)

wherein A and $R_1$ are as defined hereinbefore,
which compound of formula (IX) is reacted with a compound of formula (X):

(X)

wherein n and Ar are as defined for formula (I),
to yield, after deprotection where appropriate, a compound of formula (I),
which compound of formula (I) is purified, if necessary, according to a conventional purification technique, separated, if desired, into its isomers according to a conventional separation technique, and converted, if desired, into its isomers, N-oxydes and pharmaceutically-acceptable acid or base addition salts thereof The compounds of formula (II) are obtained by benzylation of the corresponding acids.

In addition to the fact that the compounds of the present invention are new, they have especially valuable pharmacological properties.

They are potent inhibitors of trypsin-related serine proteases, exhibiting significant selectivity in respect of thrombin compared with other coagulation and fibrinolysis serine proteases.

Those properties make them useful in the treatment of stable or unstable angina, disorders of thrombotic origin and/or giving rise to thrombotic complications, in the treatment or prevention of myocardial infarction and venous or arterial thromboses, and in the treatment of complications of vascular and cardiovascular diseases, such as atherosclerosis, arteritis, venous disorder, and in the treatment of any disorders involving thrombin formation and/or activity.

They may also be used in therapeutic association with a thrombolytic.

The invention relates also to pharmaceutical compositions comprising as active ingredient a compound of formula (I) together with one or more suitable inert, non-toxic excipients. Among the pharmaceutical compositions according to the invention there may be mentioned more especially those that are suitable for oral, parenteral (intravenous or subcutaneous) or nasal administration, tablets or dragees, sublingual tablets, gelatin capsules, lozenges, suppositories, creams, ointments, dermal gels, injectable preparations, drinkable suspensions, etc.

The useful dosage can be adapted according to the nature and severity of the disorder, the route of administration and the age and weight of the patient. The dosage varies from 1 to 500 mg per day in one or more administrations.

The following Examples illustrate the invention but do not limit it in any way.

A compound of configuration (2α) or (2β) is understood to mean a compound selected from the (2R) and (2S) stereoisomers, it being understood that when the (2α) compound represents one of the (2R) or (2S) stereoisomers, the (2β) compound represents the other stereoisomer, the absolute configuration of the carbon atom in position 2 being undefined.

The starting materials used are known or are prepared according to known procedures.

Preparations A to G yield synthesis intermediates for use in the preparation of the compounds of the invention. The structures of the compounds described in the Examples were determined according to the usual spectrophotometric techniques (infrared, NMR, mass spectrometry).

PREPARATION A: 3-Aminomethyl-6-tert-butyloxycarbonylamino-2-methylpyridine

Step A: 6-Amino-3-cyano-2-methylpyridine

Copper(I) cyanide (12 mmol) is added to 10 mmol of 6-amino-3-bromo-2-methylpyridine dissolved in dimethylformamide. The mixture is refluxed for 10 hours, and then cooled to 80° C. and poured into a solution of sodium cyanide (40 mmol) in water. After stirring for 1 hour at room temperature, the mixture is extracted with ethyl acetate. The organic phase is washed, then dried and evaporated to yield the expected product in the form of an ochre solid.

Step B: 6-Tert-butyloxycarbonylamino-3-cyano-2-methylpyridine

A solution of 1N sodium hydroxide (11 mmol) and di-tert-butyl dicarbonate (11 mmol) is added to 10 mmol of the compound described in the preceding Step dissolved in tert-butanol. After stirring for 1 hour, the solvents are removed by evaporation, the residue is taken up in ethyl acetate, and the organic phase is washed, dried and evaporated to yield the expected product.

Step C: 6-Tert-butyloxycarbonylamino-3-aminomethyl-2-methylpyridine

A solution of the compound described in the preceding Step (10 mmol) in ethanol is placed under hydrogen overnight in the presence of Raney nickel. After removal of the catalyst by filtration, the solvent is removed by evaporation to yield the expected product.

PREPARATION B: 3-Aminomethyl-6-tert-butyloxycarbonylamino-2,5-dimethylpyridine

The expected product is obtained according to the process described in Preparation A starting from 6-amino-3-bromo-2,5-dimethylpyridine.

PREPARATION C: 3-Aminomethyl-6-tert-butyloxycarbonylamino-2,4-dimethylpyridine

The expected product is obtained according to the process described in Preparation A starting from 6-amino-3-bromo-2,4-dimethylpyridine.

PREPARATION D: 3-Aminomethyl-6-tert-butyloxycarbonylamino-2-ethylpyridine

The expected product is obtained according to the process described in Preparation A starting from 6-amino-3-bromo-2-ethylpyridine.

PREPARATION E: 2-[2-(Aminomethyl)phenoxy]-N-ethylacetamide

Step A: 2-(2-Cyanophenoxy)ethyl acetate

Potassium carbonate (30 mmol) and then ethyl acetate (11 mmol) are added to a solution of 2-hydroxybenzonitrile (10 mmol) in acetonitrile. After stirring overnight, the solution is filtered and evaporated, the residue is taken up in ethyl acetate, and the organic phase is washed, dried and then evaporated to yield the expected product.

Step B: 2-[2-Cyanophenoxy] acetic acid

Sodium hydroxide 1N (11 mmol) is added to a solution, at 0° C., of the compound obtained in the preceding Step (10 mmol) in tetrahydrofurane. After stirring overnight, the mixture is evaporated and the residue is taken up in water. The organic phase is washed with ethyl acetate and acidified by hydrochloric acid 4N. The resulting precipitate is filtered and dried.

Step C: 2-[2-Cyanophenoxy]-N-ethylacetamide

N-hydroxysuccinimide (11 mmol) and N,N'-dicyclohexylcarbodiimide (11 mmol) are added to a solution of the compound described in preceding step (10 mmol) in dimethylformamide. After stirring 2 hours at room temperature, ethylamine (11 mmol) is added. After stirring overnight, the mixture is evaporated, filtered and taken up in ethyl acetate. The organic phase is washed with water and dried. The expected product is obtained after evaporation.

Step D: 2-[2-(Aminomethyl)phenoxy]-N-ethylacetamide

The expected product is obtained according to the process described in Step C of Preparation A starting from the compound obtained in the preceding Step.

PREPARATION F: 2-[2-(Aminomethyl)-4-chlorophenoxy]-N-ethylacetamide

The expected product is obtained according to the process described in Preparation E, replacing 2-hydroxybenzonitrile by 5-chloro-2-hydroxybenzonitrile.

PREPARATION G: 3-Aminomethyl-6-tert-butyloxycarbonylamino-2-hydroxymethylpyridine The expected product is obtained according to the process described in Preparation A starting from 6-amino-3-bromo-2-hydroxymethylpyridine.

EXAMPLE 1

(6S)-N-[(6-Amino-2-methyl-3-pyridyl)methyl]-4-oxo-3-(2-phenethylamino)-4,6,7,8-tetrahydropyrrolo[1,2-a]pyrazine-6-carboxamide dihydrochloride Step A: Benzyl (2S)-N-tert-butoxycarbonyl-5-oxoprolinate 11 mmol of dimethylaminopyridine and 11 mmol of di-tert-butyl dicarbonate are added at 0° C. to 10 mmol of benzyl (2S)-5-oxoprolinate (the preparation process of which is described by E. Campaigne et al. (J. Heterocycl. Chem. 1975, 12, 391)) dissolved in dichloromethane. After 24 hours' stirring at room temperature, the reaction mixture is washed and then dried and evaporated to yield the expected product in the form of a viscous oil.

Step B: Benzyl (2S)-N-tert-butoxycarbonyl-5-hydroxyprolinate 18 mmol of a 1M solution of diisobutylaluminium hydride in hexane are added, under argon at −78° C., to 10 mmol of the compound obtained in the preceding Step dissolved in tetrahydrofuran. After 20 minutes' stirring at −78° C., an aqueous saturated ammonium chloride solution and then an aqueous 10% sodium carbonate solution are added. After stirring overnight at room temperature, the reaction mixture is filtered, and the filtrate is evaporated and taken up in dichloromethane. The organic phase is washed, dried and then evaporated. The residue is purified by chromatography over silica gel using a dichloromethane/ethyl acetate mixture, 95/5, as eluant. The expected product is obtained in the form of a yellow oil.

Step C: Benzyl (2S)-N-tert-butoxycarbonyl-5-methoxyprolinate

A solution of 0.1% para-toluenesulphonic acid in anhydrous methanol (88 ml) is added to 10 mmol of the compound obtained in the preceding Step. After stirring for ½ hour, an aqueous 10% sodium carbonate solution is added, and the product is extracted with dichloromethane. The expected product is obtained in the form of a slightly yellow oil.

Step D: Benzyl (2S)-5-cyanoprolinate hydrochloride

A solution of tin tetrachloride in 5% v/v anhydrous dichloromethane (7.1 ml) and then trimethylsilyl cyanide (20.6 mmol) are added, at −40° C. under argon, to 10 mmol of the compound obtained in the preceding Step. After stirring for 2 hours at −40° C., an aqueous 10% sodium carbonate solution is added, the aqueous phase is extracted with dichloromethane, and the organic phase is washed, dried and then evaporated. The resulting residue is purified by chromatography over silica gel using a dichloromethane/ethyl acetate mixture, 95/5, as eluant. The resulting yellow oil is dissolved in ethyl acetate and then a stream of hydrogen chloride gas is passed through at 0° C. for 30 minutes. After stirring overnight at room temperature, the precipitate that forms is filtered, rinsed with ethyl acetate and dried in vacuo using a dessicator.

Step E: Benzyl (6S)-1,3-dichloro-4-oxo-4,6,7,8-tetrahydropyrrolo[1,2-a]pyrazine-6-carboxylate Oxalyl chloride (40 mmol) is added to 10 mmol of the compound obtained in the preceding Step dissolved in ortho-dichlorobenzene. After stirring for 15 hours at 100° C., the mixture is returned to room temperature and the solvents are removed by evaporation. The resulting residue is purified by chromatography over silica gel using a dichloromethane/ethyl acetate mixture, 95/5, as eluant. The expected product is obtained in the form of a beige solid.

Step F: Benzyl (6S)-1-chloro-4-oxo-3-(2-phenethylamino)-4,6,7,8-tetrahydropyrrolo[1,2-a]pyrazine-6-carboxylate 30 mmol of 2-phenethylamine are added to 10 mmol of the compound obtained in the preceding Step dissolved in ethyl acetate. After stirring for 2 hours at reflux, the reaction mixture is returned to room temperature and ethyl acetate is added. The organic phase is washed, dried and then evaporated. The resulting residue is purified by chromatography over silica gel using a dichloromethane/ethyl acetate mixture as eluant. The resulting product is obtained in the form of a white solid.

Step G: (6S)-1-Chloro-4-oxo-3-(2-phenethylamino)-4,6,7,8-tetrahydropyrrolo[1,2-a]pyrazine-6-carboxylic acid 42 mg of 10% Pd/C are added to 10 mmol of the compound obtained in the preceding Step dissolved in dioxane. The mixture is placed under hydrogen for 5 hours at ambient pressure and temperature. After removal of the catalyst by filtration, the solvent is removed by evaporation to yield the expected product in the form of a white solid.

Step H: (6S)-4-Oxo-3-(2-phenethylamino)-4,6,7,8-tetrahydropyrrolo[1,2-a]pyrazine-6-carboxylic acid A 1N sodium hydroxide solution (20 mmol) is added to 10 mmol of the compound obtained in the preceding Step dissolved in dioxane. The mixture is placed under hydrogen overnight at ambient pressure and temperature in the presence of 10% Pd/C (42 mg). After removal of the catalyst by filtration, the solvent is removed by evaporation and the residue is taken up in water and then rendered acidic with $KHSO_4$. The precipitate is filtered off and then dried in vacuo using a dessicator in the presence of $P_2O_5$. The expected product is obtained in the form of a white solid.

Step I: (6S)-N-[(6-Amino-2-methyl-3-pyridyl)methyl]-4-oxo-3-(2-phenethylamino)-4,6,7,8-tetrahydropyrrolo[1,2-a]pyrazine-6-carboxamide dihydrochloride 11 mmol of O-(1H-benzotriazol-1-yl)-N,N,N'N'-tetramethyluronium tetrafluoroborate and 11 mmol of diiso-propylethylamine are added to 10 mmol of the compound obtained in the preceding Step and 11 mmol of the compound described in Preparation A dissolved in dimethylformamide. After stirring overnight at room temperature, the solvent is removed by evaporation. The resulting residue is taken up in ethyl acetate. The organic phase is washed, dried and then evaporated. The resulting residue is dissolved in ethyl acetate and then a stream of hydrogen chloride gas is passed through at 0° C. for 30 minutes. After stirring overnight at room temperature, the precipitate that forms is filtered off, rinsed with ethyl acetate and dried in vacuo using a dessicator.

Elemental Microanalysis

| | %C | %H | %N | %Cl |
|---|---|---|---|---|
| Calculated: | 56.22 | 5.74 | 17.10 | 14.43 |
| Found: | 56.93 | 5.73 | 17.34 | 14.60 |

EXAMPLE 2

(6R)-N-[(6-Amino-2-methyl-3-pyridyl)methyl]-4-oxo-3-(2-phenethylamino)-4,6,7,8-tetrahydropyrrolo[1,2-a]pyrazine-6-carboxamide dihydrochloride The expected product is obtained starting from benzyl (2R)-5-oxoprolinate according to the process described in Example 1.

EXAMPLE 3

N-[(6-Amino-2-methyl-3-pyridyl)methyl]-4-oxo-3-(2-phenethylamino)-4,6,7,8-tetrahydropyrrolo[1,2-a]pyrazine-6-carboxamide dihydrochloride The expected product is obtained starting from benzyl (±)-5-oxoprolinate according to the process described in Example 1.

EXAMPLE 4

(6S)-N-[(6-Amino-2-methyl-3-pyridyl)methyl]-4-oxo-3-(2-phenethylamino)-6,7,8,9-tetrahydro-4H-pyrido[1,2-a]pyrazine-6-carboxamide dihydrochloride The expected product is obtained according to the process described in Example 1 starting from benzyl (2S)-6-oxo-2-piperidinecarboxylate.

EXAMPLE 5

(3S)-N-[(6-Amino-2-methyl-3-pyridyl)methyl]-5-oxo-6-(2-phenethylamino)-2,3-dihydro-5H-[1,3]thiazolo[3,2-a]pyrazine-3-carboxamide dihydrochloride The expected product is obtained according to the process described in Example 1 starting from benzyl (4R)-2-oxo-1,3-thiazolidine-4-carboxylate.

EXAMPLE 6

(6S)-N-[(6-Amino-2-methyl-3-pyridyl)methyl]-3-[(2,2-diphenylethyl)amino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 2,2-diphenylethylamine and the compound described in Preparation A.

Elemental Microanalysis

|  | %C | %H | %N | %Cl |
|---|---|---|---|---|
| Calculated: | 61.38 | 5.68 | 14.81 | 12.49 |
| Found: | 61.97 | 5.76 | 15.10 | 12.41 |

EXAMPLE 7

(6S)-N-[(6-Amino-2-methyl-3-pyridyl)methyl]-3-[(3,4-dimethoxyphenethyl)amino]-4-oxo-4,6,7,8-tetrahydropyrrolo[1,2-a]pyrazine-6-carboxamide dihydrochloride monohydrate The expected product is obtained according to the process described in Steps F to I of Example 1, starting from the compound described in Step E of Example 1, 3,4-dimethoxyphenethylamine and the compound described in Preparation A.

Elemental Microanalysis

|  | %C | %H | %N | %Cl |
|---|---|---|---|---|
| Calculated: | 52.73 | 6.02 | 14.76 | 12.45 |
| Found: | 53.39 | 6.26 | 14.70 | 13.00 |

EXAMPLE 8

(6S)-N-[(6-Amino-2-methyl-3-pyridyl)methyl]-4-oxo-3-[(2-(4-pyridyl)ethyl)amino]-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, 4-(2-aminoethyl)pyridine and the compound described in Preparation A.

EXAMPLE 9

(6S)-N-[(6-Amino-2-methyl-3-pyridyl)methyl]-3-[(2-cyclohexylethyl)amino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 2-cyclohexylethylamine and the compound described in Preparation A.

EXAMPLE 10

(2R)-N-[(6S)-6-{5[((6-Amino-2-methyl-3-pyridyl)methyl)amino]carbonyl}-4-oxo-4,6,7,8-tetrahydropyrrolo[1,2-a]pyrazin-3-yl]phenylalanine hydrochloride The expected product is obtained according to the process described in Steps F to I of Example 1, starting from the compound described in Step E of Example 1, (2R)-phenylalanine tert-butyl ester and the compound described in Preparation A.

EXAMPLE 11

(3S)-N-[(6-Amino-2-methyl-3-pyridyl)methyl]-5-oxo-6-(2-phenethylamino)-2,3-dihydro-5H-[1,3]oxazolo[3,2-a]pyrazine-3-carboxamide dihydrochloride The expected product is obtained according to the process described in Example 1 starting from benzyl (4R)-2-oxo-1,3-oxazolidine-4-carboxylate, the preparation of which is described in Tet. Lett. 1995, 36 (37), 6595–6598.

EXAMPLE 12

(6S)-N-[(6-Amino-2-methyl-3-pyridyl)methyl]-3-benzylamino-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, benzylamine and the compound described in Preparation A.

Elemental Microanalysis

|  | %C | %H | %N | %Cl |
|---|---|---|---|---|
| Calculated: | 55.35 | 5.49 | 17.60 | 14.85 |
| Found: | 55.97 | 5.33 | 17.62 | 14.47 |

EXAMPLE 13

(6S)-N-[(6-Amino-2-methyl-3-pyridyl)methyl]-4-oxo-3-(3-phenylpropylamino)-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 3-phenylpropylamine and the compound described in Preparation A.

Elemental Microanalysis

|  | %C | %H | %N | %Cl |
|---|---|---|---|---|
| Calculated: | 57.03 | 5.98 | 16.63 | 14.03 |
| Found: | 57.23 | 5.94 | 16.45 | 14.32 |

EXAMPLE 14

(6S)-N-[(6-Amino-2-methyl-3-pyridyl)methyl]-3-diphenylmethylamino-4-oxo-4,6,7,8-tetrahydropyrrolo[1,2-a] pyrazine-6-carboxamide dihydrochloride The expected product is obtained according to the process described in Steps F to I of Example 1, starting from the compound described in Step E of Example 1, diphenylmethylamine and the compound described in Preparation A.

Elemental Microanalysis

|  | %C | %H | %N | %Cl |
|---|---|---|---|---|
| Calculated: | 60.76 | 5.46 | 15.18 | 12.81 |
| Found: | 60.59 | 5.53 | 15.11 | 13.62 |

EXAMPLE 15

(6S)-N-[(6-Amino-2-methyl-3-pyridyl)methyl]-4-oxo-3-[2-(2-pyridyl)ethylamino]-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, 2-(2-pyridyl)ethylamine and the compound described in Preparation A.

Elemental Microanalysis

|  | %C | %H | %N | %Cl |
|---|---|---|---|---|
| Calculated: | 49.96 | 5.34 | 18.54 | 20.11 |
| Found: | 50.27 | 5.23 | 18.46 | 20.08 |

EXAMPLE 16

(6S)-N-[(6-Amino-2-methyl-3-pyridyl)methyl]-4-oxo-3-[2-(3-pyridyl)ethylamino]-4,6,7,8-tetrahydropyrrolo[1,2-a]pyrazine-6-carboxamide trihydrochloride The expected product is obtained according to the process described in Steps F to I of Example 1, starting from the compound described in Step E of Example 1,2-(3-pyridyl)-ethylamine and the compound described in Preparation A.

Elemental Microanalysis

|  | %C | %H | %N | %Cl |
|---|---|---|---|---|
| Calculated: | 49.96 | 5.34 | 18.54 | 20.11 |
| Found: | 49.13 | 5.32 | 18.08 | 20.00 |

EXAMPLE 17

(6S)-N-[(6-Amino-2-methyl-3-pyridyl)methyl]-3-(indan-2-yl-methylamino)-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, indan-2-yl-methylamine and the compound described in Preparation A.

Elemental Microanalysis

|  | %C | %H | %N | %Cl |
|---|---|---|---|---|
| Calculated: | 58.03 | 5.84 | 16.24 | 13.70 |
| Found: | 57.90 | 5.69 | 16.20 | 13.05 |

EXAMPLE 18

(6S)-N-[(6-Amino-2-methyl-3-pyridyl)methyl]-3-[(1,1'-biphenyl)-4-yl-methylamino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, (1,1'-biphenyl)-4-yl-methylamine and the compound described in Preparation A.

EXAMPLE 19

(6S)-N-[(6-Amino-2-methyl-3-pyridyl)methyl]-3-(2-methyl-2-phenylpropylamino)-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 2-methyl-2-phenylpropylamine and the compound described in Preparation A.

Elemental Microanalysis

|  | %C | %H | %N | %Cl |
|---|---|---|---|---|
| Calculated: | 57.80 | 6.21 | 16.18 | 13.65 |
| Found: | 57.29 | 6.49 | 15.93 | 14.22 |

EXAMPLE 20

(6S)-N-[(6-Amino-2-methyl-3-pyridyl)methyl]-4-oxo-3-[(2α)-2-(2-pyridyl)-2-phenethylamino]-4,6,7,8-tetrahydropyrrolo[1,2-a]pyrazine-6-carboxamide trihydrochloride Step A: (2α)-2-(2-Pyridyl)-2-phenethylamine The expected product is obtained by resolution of (±)-2-(2-pyridyl)-2-phenethylamine (described in J. Am. Chem. Soc. 1971, 93, 5542) using D-dibenzoyl-tartaric acid.

Step B: (6S)-N-[(6-Amino-2-methyl-3-pyridyl)methyl]-4-oxo-3-[(2α)-2-(2-pyridyl)-2-phenethylamino]-4,6,7,8-tetrahydropyrrolo[1,2-a]-pyrazine-6-carboxamide trihydrochloride The expected product is obtained according to the process described in Steps F to I of Example 1, starting from the compound described in Step E of Example 1, the compound obtained in the preceding Step and the compound described in Preparation A.

Elemental Microanalysis

|  | %C | %H | %N | %Cl |
|---|---|---|---|---|
| Calculated: | 55.59 | 5.33 | 16.21 | 17.58 |
| Found: | 54.83 | 5.46 | 15.83 | 18.41 |

EXAMPLE 21

(6S)-N-[(6-Amino-2-methyl-3-pyridyl)methyl]-4-oxo-3-[(2β)-2-(2-pyridyl)-2-phenethylamino]-4,6,7,8-tetrahydropyrrolo[1,2-a]-pyrazine-6-carboxamide trihydrochloride The expected product is obtained according to the process described in Steps F to I of Example 1, starting from the compound described in Step E of Example 1, (2β)-2-(2-pyridyl)-2-phenethylamine and the compound described in Preparation A.

EXAMPLE 22

(6S)-N-[(6-Amino-2-methyl-3-pyridyl)methyl]-3-[2,2-di-(2-pyridyl)ethylamino]-4-oxo-4,6,7,8-tetrahydropyrrolo[1,2-a]pyrazine-6-carboxamide tetrahydrochloride The expected product is obtained according to the process described in Steps F to I of Example 1, starting from the compound described in Step E of Example 1, 2,2-di-(2-pyridyl)ethylamine and the compound described in Preparation A.

Elemental Microanalysis

|  | %C | %H | %N | %Cl |
|---|---|---|---|---|
| Calculated: | 50.48 | 5.02 | 17.44 | 22.07 |
| Found: | 50.73 | 5.18 | 17.28 | 22.56 |

EXAMPLE 23

(6S)-N-[(6-Amino-2-methyl-3-pyridyl)methyl]-3-[2,2-bis-(4-methoxy-phenyl)ethylamino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 2,2-bis-(4-methoxyphenyl)ethylamine and the compound described in Preparation A.

EXAMPLE 24

(6S)-N-[(6-Amino-2-methyl-3-pyridyl)methyl]-3-[2,2-bis-(4-hydroxy-phenyl)ethylamino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 2,2-bis-(4-hydroxyphenyl)ethylamine and the compound described in Preparation A.

EXAMPLE 25

(6S)-N-[(6-Amino-2-methyl-3-pyridyl)methyl]-3-[2,2-bis-(4-chlorophenyl)ethylamino]-4-oxo-4,6,7,8-tetrahydropyrrolo[1,2-a]-pyrazine-6-carboxamide dihydrochloride The expected product is obtained according to the process described in Steps F to I of Example 1, starting from the compound described in Step E of Example 1, 2,2-bis-(4-chlorophenyl)ethylamine and the compound described in Preparation A.

EXAMPLE 26

(6S)-N-[(6-Amino-2-methyl-3-pyridyl)methyl]-3-[2,2-di-(p-tolyl)-ethylamino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 2,2-di-(p-tolyl)-ethylamine and the compound described in Preparation A.

EXAMPLE 27

(6S)-N-[(6-Amino-2-methyl-3-pyridyl)methyl]-3-[2,2-bis-(4-fluorophenyl)ethylamino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 2,2-bis-(4-fluorophenyl)ethylamine and the compound described in Preparation A.

EXAMPLE 28

(6S)-N-[(6-Amino-2-methyl-3-pyridyl)methyl]-3-[2,2-dicyclohexyl-ethylamino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 2,2-dicyclohexylethylamine and the compound described in Preparation A.

Elemental Microanalysis

|  | %C | %H | %N | %Cl |
|---|---|---|---|---|
| Calculated: | 60.10 | 7.65 | 14.39 | 12.23 |
| Found: | 60.27 | 7.67 | 14.50 | 12.29 |

EXAMPLE 29

(6S)-N-[(6-Amino-2-methyl-3-pyridyl)methyl]-3-[2,2-bis-(2,4-difluorophenyl)ethylamino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 2,2-bis-(2,4-difluorophenyl)ethylamine and the compound described in Preparation A.

EXAMPLE 30

(6S)-N-[(6-Amino-2-methyl-3-pyridyl)methyl]-3-[2,2-bis-(2,6-dimethylphenyl)ethylamino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 2,2-bis-(2,6-dimethylphenyl)ethylamine and the compound described in Preparation A.

EXAMPLE 31

(6S)-N-[(6-Amino-2-methyl-3-pyridyl)methyl]-3-[2,2-bis-(6-ethyl-2-pyridyl)ethylamino]-4-oxo-4,6,7,8-tetrahydropyrrolo[1,2-a]pyrazine-6-carboxamide tetrahydrochloride The expected product is obtained according to the process described in Steps F to I of Example 1, starting from the compound described in Step E of Example 1, 2,2-bis-(6-ethyl-2-pyridyl)ethylamine and the compound described in Preparation A.

EXAMPLE 32

(6S)-N-[(6-Amino-2-methyl-3-pyridyl)methyl]-4-oxo-3-[(2R)-2-(1-naphthyl)-2-(2-pyridyl)ethylamino]-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, (2R)-2-(1-naphthyl)-2-(2-pyridyl)ethylamine and the compound described in Preparation A.

EXAMPLE 33

(6S)-N-[(6-Amino-2-methyl-3-pyridyl)methyl]-4-oxo-3-[(2S)-2-(1-naphthyl)-2-(2-pyridyl)ethylamino]-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, (2S)-2-(1-naphthyl)-2-(2-pyridyl)ethylamine and the compound described in Preparation A.

EXAMPLE 34

(6S)-N-[(6-Amino-2-methyl-3-pyridyl)methyl]-4-oxo-3-[(2R)-2-(2-naphthyl)-2-(2-pyridyl)ethylamino]-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, (2R)-2-(2-naphthyl)-2-(2-pyridyl)ethylamine and the compound described in Preparation A.

EXAMPLE 35

(6S)-N-[(6-Amino-2-methyl-3-pyridyl)methyl]-4-oxo-3-[(2S)-2-(2-naphthyl)-2-(2-pyridyl)ethylamino]-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, (2S)-2-(2-naphthyl)-2-(2-pyridyl)ethylamine and the compound described in Preparation A.

EXAMPLE 36

(6S)-N-[(6-Amino-2-methyl-3-pyridyl)methyl]-4-oxo-3-[(2R)-2-(2-pyridyl)-2-phenylbutylamino]-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, (2R)-2-(2-pyridyl)-2-phenylbutylamine and the compound described in Preparation A.

EXAMPLE 37

(6S)-N-[(6-Amino-2-methyl-3-pyridyl)methyl]-4-oxo-3-[(2S)-2-(2-pyridyl)-2-phenylbutylamino]-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, (2S)-2-(2-pyridyl)-2-phenylbutylamine and the compound described in Preparation A.

EXAMPLE 38

(6S)-N-[(6-Amino-2-methyl-3-pyridyl)methyl]-3-[(9H-fluoren-9-yl)methylamino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, (9H-fluoren-9-yl)methylamine and the compound described in Preparation A.

EXAMPLE 39

(6S)-N-[(6-Amino-2-methyl-3-pyridyl)methyl]-3-[(9,10-dihydro-9-anthryl)methylamino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, (9,10-dihydro-9-anthryl)methylamine and the compound described in Preparation A.

EXAMPLE 40

(6S)-N-[(6-Amino-2-methyl-3-pyridyl)methyl]-3-[(10,11-dihydro-5H-dibenzo[a,d]cyclohepten-5-yl)methylamino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, (10,11-dihydro-5H-dibenzo[a,d]cyclohepten-5-yl)methylamine and the compound described in Preparation A.

Elemental Microanalysis

|  | %C | %H | %N | %Cl |
|---|---|---|---|---|
| Calculated: | 62.73 | 5.77 | 14.16 | 11.95 |
| Found: | 63.02 | 5.83 | 14.09 | 11.49 |

EXAMPLE 41

(6S)-N-[(6-Amino-2-methyl-3-pyridyl)methyl]-4-oxo-3-[(9H-xanthen-9-yl)methylamino]-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, (9H-xanthen-9-yl)methylamine and the compound described in Preparation A.

EXAMPLE 42

(6S)-N-[(6-Amino-2-methyl-3-pyridyl)methyl]-4-oxo-3-[(9H-thioxanthen-9-yl)methylamino]-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, (9H-thioxanthen-9-yl)methylamine and the compound described in Preparation A.

EXAMPLE 43

(6S)-N-[(6-Amino-2-methyl-3-pyridyl)methyl]-3-[(10-methyl-9,10-dihydro-9-acridinyl)methylamino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, (10-methyl-9,10-dihydro-9-acridinyl)methylamine and the compound described in Preparation A.

EXAMPLE 44

(6S)-N-[(6-Amino-2-methyl-3-pyridyl)methyl]-3-[(9H-indeno-[2,1-b]pyridin-9-yl)methylamino]-4-oxo-4,6,7,8-tetrahydropyrrolo-[1,2-a]pyrazine-6-carboxamide trihydrochloride The expected product is obtained according to the process described in Steps F to I of Example 1, starting from the compound described in Step E of Example 1, (9H-indeno-[2,1-b]pyridin-9-yl)methylamine and the compound described in Preparation A.

EXAMPLE 45

(6S)-N-[(6-Amino-2-methyl-3-pyridyl)methyl]-3-[(5,10-dihydrobenzo[g]quinolin-10-yl)methylamino]-4-oxo-4,6,7,8-tetrahydro-pyrrolo[1,2-a]pyrazine-6-carboxamide trihydrochloride The expected product is obtained according to the process described in Steps F to I of Example 1, starting from the compound described in Step E of Example 1, (5,10-dihydrobenzo[g]quinolin-10-yl)methylamine and the compound described in Preparation A.

EXAMPLE 46

(6S)-N-[(6-Amino-2-methyl-3-pyridyl)methyl]-3-[(6,11-dihydro-5H-benzo[5,6]cyclohepta[1,2-b]pyridin-11-yl)methylamino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, (6,11-dihydro-5H-benzo[5,6]cyclohepta[1,2-b]pyridin-11-yl)methylamine and the compound described in Preparation A.

EXAMPLE 47

(6S)-N-[(6-Amino-2-methyl-3-pyridyl)methyl]-3-[(10,11-dihydro-4,6-diaza-5H-dibenzo[a,d]cyclohepten-5-yl)methylamino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, (10,11-dihydro-4,6-diaza-5H-dibenzo[a,d]cyclohepten-5-yl)methylamine and the compound described in Preparation A.

EXAMPLE 48

(6S)-N-[(6-Amino-2-methyl-3-pyridyl)methyl]-4-oxo-3-[2-5-phenyl-2-pyridyl)ethylamino]-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 2-(5-phenyl-2-pyridyl)ethylamine and the compound described in Preparation A.

EXAMPLE 49

(6S)-N-[(6-Amino-2-methyl-3-pyridyl)methyl]-4-oxo-3-[2-(5-butyl-2-pyridyl)ethylamino]-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, 2-(5-butyl-2-pyridyl)ethylamine and the compound described in Preparation A.

EXAMPLE 50

(6S)-N-[(6-Amino-2-methyl-3-pyridyl)methyl]-3-[2-(1-naphthyl)ethylamino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 2-(1-naphthyl)ethylamine and the compound described in Preparation A.

Elemental Microanalysis

|  | %C | %H | %N | %Cl |
|---|---|---|---|---|
| Calculated: | 59.89 | 5.58 | 15.52 | 13.09 |
| Found: | 60.47 | 5.84 | 15.57 | 12.76 |

EXAMPLE 51

(6S)-N-[(6-Amino-2-methyl-3-pyridyl)methyl]-3-[2-(2-naphthyl)ethylamino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 2-(2-naphthyl)ethylamine and the compound described in Preparation A.

Elemental Microanalysis

|  | %C | %H | %N | %Cl |
|---|---|---|---|---|
| Calculated: | 59.89 | 5.58 | 15.52 | 13.09 |
| Found: | 60.66 | 5.71 | 15.65 | 12.58 |

EXAMPLE 52

(6S)-N-[(6-Amino-2-methyl-3-pyridyl)methyl]-4-oxo-3-[2-(5-ethoxy-6-methyl-2-pyridyl)ethylamino]-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 2-(5-ethoxy-6-methyl-2-pyridyl)ethylamine and the compound described in Preparation A.

Elemental Microanalysis

|  | %C | %H | %N | %Cl |
|---|---|---|---|---|
| Calculated: | 54.55 | 6.04 | 17.81 | 12.88 |
| Found: | 55.70 | 6.13 | 17.71 | 13.18 |

EXAMPLE 53

(6S)-N-[(6-Amino-2-methyl-3-pyridyl)methyl]-4-oxo-3-[2-(6,7-dihydro-5H-cyclopenta[b]pyridin-2-yl)ethylamino]-4,6,7,8tetrahydropyrrolo[1,2-a]pyrazine-6-carboxamide trihydrochloride The expected product is obtained according to the process described in Steps F to I of Example 1, starting from the compound described in Step E of Example 1, 2-(6,7-dihydro-5H-cyclopenta[b]pyridin-2-yl)ethylamine and the compound described in Preparation A.

EXAMPLE 54

(6S)-N-[(6-Amino-2-methyl-3-pyridyl)methyl]-3-[1,3-di-(2-pyridyl)-2-propanamino]-4-oxo-4,6,7,8-tetrahydropyrrolo[1,2-a]pyrazine-6-carboxamide tetrahydrochloride The expected product is obtained according to the process described in Steps F to I of Example 1, starting from the compound described in Step E of Example 1, 1,3-di-(2-pyridyl)-2-propanamine and the compound described in Preparation A.

EXAMPLE 55

(6S)-N-[(6-Amino-2-methyl-3-pyridyl)methyl]-3-[1,3-diphenyl-2-propanamino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 1,3-diphenyl-2-propanamine and the compound described in Preparation A.

EXAMPLE 56

(6S)-N-[(6-Amino-2-methyl-3-pyridyl)methyl]-3-[(2α)-3,3,3-trifluoro-2-phenyl-1-propanamino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, (2α)-3,3,3-trifluoro-2-phenyl-1-propanamine and the compound described in Preparation A.

EXAMPLE 57

(6S)-N-[(6-Amino-2-methyl-3-pyridyl)methyl]-3-[(2β)-3,3,3-trifluoro-2-phenyl-1-propanamino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, (2β)-3,3,3-trifluoro-2-phenyl-1-propanamine and the compound described in Preparation A.

EXAMPLE 58

(6S)-N-[(6-Amino-2-methyl-3-pyridyl)methyl]-3-[(2R)-3,3,3-trifluoro-2-cyclohexyl-l-propanamino]-4-oxo-4,6,7,8-tetrahydropyrrolo-[1,2-a]pyrazine-6-carboxamide dihydrochloride The expected product is obtained according to the process described in Steps F to I of Example 1, starting from the compound described in Step E of Example 1, (2R)-3,3,3-trifluoro-2-cyclohexyl-1-propanamine and the compound described in Preparation A.

EXAMPLE 59

(6S)-N-[(6-Amino-2-methyl-3-pyridyl)methyl]-3-[(2S)-3,3,3-trifluoro-2-cyclohexyl-1-propanamino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, (2S)-3,3,3-trifluoro-2-cyclohexyl-1-propanamine and the compound described in Preparation A.

EXAMPLE 60

(6S)-N-[(6-Amino-2-methyl-3-pyridyl)methyl]-3-(2-indanamino)-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 2-indanamine and the compound described in Preparation A.

Elemental Microanalysis

|  | %C | %H | %N | %Cl |
|---|---|---|---|---|
| Calculated: | 57.26 | 5.61 | 16.69 | 14.08 |
| Found: | 57.75 | 5.54 | 16.72 | 14.07 |

EXAMPLE 61

(6S)-N-[(6-Amino-2-methyl-3-pyridyl)methyl]-3-(1-phenyl-3-azetidinamino)-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 1-phenyl-3-azetidinamine and the compound described in Preparation A.

EXAMPLE 62

(6S)-N-[(6-Amino-2-methyl-3-pyridyl)methyl]-3-(1-benzhydryl-3-azetidinamino)-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 1-benzhydryl-3-azetidinamine and the compound described in Preparation A.

EXAMPLE 63

(6S)-N-[(6-Amino-2-methyl-3-pyridyl)methyl]-3-(1-(2-naphthyl)-3-azetidinamino)-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 1-(2-naphthyl)-3-azetidinamine and the compound described in Preparation A.

EXAMPLE 64

(6S)-N-[(6-Amino-2-methyl-3-pyridyl)methyl]-3-(4,4-diphenyl-cyclohexylamino)-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 4,4-diphenylcyclohexylamine and the compound described in Preparation A.

EXAMPLE 65

(6S)-N-[(6-Amino-2,5-dimethyl-3-pyridyl)methyl]-3-(2,2-diphenylethylamino)-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 2,2-diphenylethylamine and the compound described in Preparation B.

EXAMPLE 66

(6S)-N-[(6-Amino-2,4-dimethyl-3-pyridyl)methyl]-3-(2,2-diphenylethylamino)-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 2,2-diphenylethylamine and the compound described in Preparation C.

EXAMPLE 67

(6S)-N-[(6-Amino-2-ethyl-3-pyridyl)methyl]-3-(2,2-diphenylethylamino)-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 2,2-diphenylethylamine and the compound described in Preparation D.

EXAMPLE 68

(6S)-N-[(6-Amino-2,5-dimethyl-3-pyridyl)methyl]-3-[2-(2-pyridyl)ethylamino]-4-oxo-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, 2-(2-pyridyl)ethylamine and the compound described in Preparation B.

Elemental Microanalysis

|  | %C | %H | %N | %Cl |
|---|---|---|---|---|
| Calculated: | 49.88 | 5.53 | 17.71 | 21.12 |
| Found: | 50.07 | 5.65 | 17.68 | 20.99 |

EXAMPLE 69

(6S)-N-[(6-Amino-2,4-dimethyl-3-pyridyl)methyl]-3-[2-(2-pyridyl)ethylamino]-4-oxo-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, 2-(2-pyridyl) ethylamine and the compound described in Preparation C.

EXAMPLE 70

(6S)-N-[(6-Amino-2-ethyl-3-pyridyl)methyl]-3-[2-(2-pyridyl)ethylamino]-4-oxo-4,6,7,8-tetrahydropyrrolo [1,2-a]pyrazine-6-carboxamide trihydrochloride The expected product is obtained according to the process described in Steps F to I of Example 1, starting from the compound described in Step E of Example 1, 2-(2-pyridyl) ethylamine and the compound described in Preparation D.

EXAMPLE 71

(6S)-N-[(2-Ethylcarbamoylmethoxy)benzyl]-4-oxo-3-(2-phenethylamino)-4,6,7,8-tetrahydropyrrolo [1,2-a]pyrazine-6-carboxamide The expected product is obtained according to the process described in Steps F to I of Example 1, starting from the compound described in Step E of Example 1, 2-phenethylamine and the compound described in Preparation E.

Elemental Microanalysis

|  | %C | %H | %N |
|---|---|---|---|
| Calculated: | 66.24 | 6.38 | 14.30 |
| Found: | 65.52 | 6.33 | 14.18 |

EXAMPLE 72

(6S)-N-[3-(1H-Imidazol-4-yl)propyl]-4-oxo-3-(2,2-diphenylethylamino)-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 2,2-diphenylethylamine and 3-(1H-imidazol-4-yl)propylamine described in Liebigs Ann. Chem. 1992, 317–323.

Elemental Microanalysis

|  | %C | %H | %N | %Cl |
|---|---|---|---|---|
| Calculated: | 61.34 | 5.86 | 15.33 | 11.64 |
| Found: | 61.43 | 5.83 | 14.91 | 11.97 |

EXAMPLE 73

(6S)-N-[(6-Amino-2-methyl-3-pyridyl)methyl]-3-[2,2-bis-(2-fluoro-4-methoxyphenyl)ethylamino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 2,2-bis-(2-fluoro-4-methoxyphenyl)ethylamine and the compound described in Preparation A.

EXAMPLE 74

(6S)-N-[(6-Amino-2-methyl-3-pyridyl)methyl]-3-[2,2-bis-(4-fluoro-2-methoxyphenyl)ethylamino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 2,2-bis-(4-fluoro-2-methoxyphenyl)ethylamine and the compound described in Preparation A.

EXAMPLE 75

(6S)-N-[(6-Amino-2-methyl-3-pyridyl)methyl]-3-[2,2-bis-(2-fluoro-p-tolyl)ethylamino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 2,2-bis-(2-fluoro-p-tolyl)ethylamine and the compound described in Preparation A.

EXAMPLE 76

(6S)-N-[(6-Amino-2-methyl-3-pyridyl)methyl]-4-oxo-3-[(2R)-2-(5-methyl-2-pyridyl)-2-(4-methoxyphenyl)ethylamino]-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, (2R)-2-(5-methyl-2-pyridyl)-2-(4-methoxyphenyl)ethylamine and the compound described in Preparation A.

EXAMPLE 77

(6S)-N-[(6-Amino-2-methyl-3-pyridyl)methyl]-4-oxo-3-[(2S)-2-(5-methyl-2-pyridyl)-2-(4-methoxyphenyl)ethylamino]-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, (2S)-2-(5-methyl-2-pyridyl)-2-(4-methoxyphenyl)ethylamine and the compound described in Preparation A.

EXAMPLE 78

(6S)-N-[(6-Amino-2-methyl-3-pyridyl)methyl]-4-oxo-3-[(2R)-2-(2-pyridyl)-2-(3,4-dimethylphenyl) ethylamino]-4,6,7,8-tetrahydropyrrolo[1,2-a] pyrazine-6-carboxamide trihydrochloride The expected product is obtained according to the process described in Steps F to I of Example 1, starting from the compound described in Step E of Example 1, (2R)-2-(2-pyridyl)-2-(3,4-dimethylphenyl)ethylamine and the compound described in Preparation A.

EXAMPLE 79

(6S)-N-[(6-Amino-2-methyl-3-pyridyl)methyl]-4-oxo-3-[(2S)-2-(2-pyridyl)-2-(3,4-dimethylphenyl) ethylamino]-4,6,7,8-tetrahydropyrrolo[1,2-a] pyrazine-6-carboxamide trihydrochloride The expected product is obtained according to the process described in Steps F to I of Example 1, starting from the compound described in Step E of Example 1, (2S)-2-(2-pyridyl)-2-(3,4-dimethylphenyl)ethylamine and the compound described in Preparation A.

EXAMPLE 80

(6S)-N-[(6-Amino-2-methyl-3-pyridyl)methyl]-4-oxo-3-[(2R)-2-(2-pyridyl)-2-(2,4-dimethylphenyl)ethylamino]-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, (2R)-2-(2-pyridyl)-2-(2,4-dimethylphenyl)ethylamine and the compound described in Preparation A.

EXAMPLE 81

(6S)-N-[(6-Amino-2-methyl-3-pyridyl)methyl]-4-oxo-3-[(2S)-2-(2-pyridyl)-2-(2,4-dimethylphenyl)ethylamino]-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, (2S)-2-(2-pyridyl)-2-(2,4-dimethylphenyl)ethylamine and the compound described in Preparation A.

EXAMPLE 82

(6S)-N-[(6-Amino-2-methyl-3-pyridyl)methyl]-4-oxo-3-[(2R)-2-(2-pyridyl)-2-(4-ethylphenyl)ethylamino]-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, (2R)-2-(2-pyridyl)-2-(4-ethylphenyl)ethylamine and the compound described in Preparation A.

EXAMPLE 83

(6S)-N-[(6-Amino-2-methyl-3-pyridyl)methyl]-4-oxo-3-[(2S)-2-(2-pyridyl)-2-(4-ethylphenyl)ethylamino]-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, (2S)-2-(2-pyridyl)-2-(4-ethylphenyl)ethylamine and the compound described in Preparation A.

EXAMPLE 84

(6S)-N-[(6-Amino-2-methyl-3-pyridyl)methyl]-3-[2,2-bis-(2-fluoro-4-hydroxyphenyl)ethylamino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 2,2-bis-(2-fluoro-4-hydroxyphenyl)ethylamine and the compound described in Preparation A.

EXAMPLE 85

(6S)-N-[(6-Amino-2-methyl-3-pyridyl)methyl]-3-[2,2-bis-(2,4-dimethoxyphenyl)ethylamino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 2,2-bis-(2,4-dimethoxyphenyl)ethylamine and the compound described in Preparation A.

EXAMPLE 86

(6S)-N-[(2-Ethylcarbamoylmethoxy)benzyl]-4-oxo-3-[2-(2-pyridyl)ethylamino]-4,6,7,8-tetrahydropyrrolo[1,2-a]pyrazine-6-carboxamide hydrochloride The expected product is obtained according to the process described in Steps F to I of Example 1, starting from the compound described in Step E of Example 1, 2-(2-pyridyl)ethylamine and the compound described in Preparation E.

EXAMPLE 87

(6S)-N-[(5-Chloro-2-ethylcarbamoylmethoxy)benzyl]-4-oxo-3-[2-(2-pyridyl)ethylamino]-4,6,7,8-tetrahydropyrrolo[1,2-a]pyrazine-6-carboxamide hydrochloride The expected product is obtained according to the process described in Steps F to I of Example 1, starting from the compound described in Step E of Example 1, 2-(2-pyridyl)ethylamine and the compound described in Preparation F.

EXAMPLE 88

(6S)-N-(2,5-Dichlorobenzyl)-4-oxo-3-[2-(2-pyridyl)ethylamino]-4,6,7,8-tetrahydropyrrolo[1,2-a]pyrazine-6-carboxamide hydrochloride The expected product is obtained according to the process described in Steps F to I of Example 1, starting from the compound described in Step E of Example 1, 2-(2-pyridyl)ethylamine and 2,5-dichlorobenzylamine.

EXAMPLE 89

(6S,8R)-N-[(6-Amino-2-methyl-3-pyridyl)methyl]-3-[(2,2-diphenylethyl)amino]-8-hydroxy-4-oxo-4,6,7,8-tetrahydropyrrolo[1,2-a]pyrazine-6-carboxamide dihydrochloride Step A: Benzyl (2S,4R)-4-hydroxy-5-oxo-2-pyrrolidinecarboxylate The expected product is obtained according to the process described in J. Org. Chem. 1996, 61 (14), 4838–41.

Step B: (6S,8R)-N-[(6-Amino-2-methyl-3-pyridyl)methyl]-3-[(2,2-diphenylethyl)amino]-8-hydroxy-4-oxo-4,6,7,8-tetrahydropyrrolo[1,2-a]pyrazine-6-carboxamide dihydrochloride The expected product is obtained according to the process described in Example 1, starting from the compound obtained in the preceding Step, 2,2-diphenylethylamine and the compound described in Preparation A.

EXAMPLE 90

(6S,8S)-N-[(6-Amino-2-methyl-3-pyridyl)methyl]-3-[(2,2-diphenylethyl)amino]-8-hydroxy-4-oxo-4,6,7,8-tetrahydropyrrolo[1,2-a]pyrazine-6-carboxamide dihydrochloride Step A: Benzyl (2S,4S)-4-hydroxy-5-oxo-2-pyrrolidinecarboxylate The expected product is obtained according to the process described in J. Org. Chem. 1996, 61 (14), 4838–41.

Step B: (6S,8S)-N-[(6-Amino-2-methyl-3-pyridyl) methyl]-3-[(2,2-diphenylethyl)amino]-8-hydroxy-4-oxo-4,6,7,8-tetrahydropyrrolo[1,2-a]pyrazine-6-carboxamide dihydrochloride The expected product is obtained according to the process described in Example 1, starting from the compound obtained in the preceding Step, 2,2-diphenylethylamine and the compound described in Preparation A.

EXAMPLE 91

(6S,8R)-N-[(6-Amino-2-methyl-3-pyridyl)methyl]-3-[(2,2-diphenylethyl)amino]-8-methoxy-4-oxo-4,6,7,8-tetrahydropyrrolo[1,2-a]pyrazine-6-carboxamide dihydrochloride Step A: Benzyl (2S,4R)-4-methoxy-5-oxo-2-pyrrolidinecarboxylate The expected product is obtained according to the process described in Indian. J. Chem. (B) 1996, 35 (11), 1221–24 starting from the compound described in Step A of Example 89.

Step B: (6S,8R)-N-[(6-Amino-2-methyl-3-pyridyl) methyl]-3-[(2,2-diphenylethyl)amino]-8-methoxy-4-oxo-4,6,7,8-tetrahydropyrrolo[1,2-a]pyrazine-6-carboxamide dihydrochloride The expected product is obtained according to the process described in Example 1, starting from the compound obtained in the preceding Step, 2,2-diphenylethylamine and the compound described in Preparation A.

EXAMPLE 92

(6S,8S)-N-[(6-Amino-2-methyl-3-pyridyl)methyl]-3-[(2,2-diphenylethyl)amino]-8-methoxy-4-oxo-4,6,7,8-tetrahydropyrrolo[1,2-a]pyrazine-6-carboxamide dihydrochloride Step A: Benzyl (2S,4S)-4-methoxy-5-oxo-2-pyrrolidinecarboxylate The expected product is obtained according to the process described in Indian. J. Chem. (B) 1996, 35 (11), 1221–24, starting from the compound described in Step A of Example 90.

Step B: (6S,8S)-N-[(6-Amino-2-methyl-3-pyridyl) methyl]-3-[(2,2-diphenylethyl)amino]-8-methoxy-4-oxo-4,6,7,8-tetrahydropyrrolo[1,2-a]pyrazine-6-carboxamide dihydrochloride The expected product is obtained according to the process described in Example 1, starting from the compound obtained in the preceding Step, 2,2-diphenylethylamine and the compound described in Preparation A.

EXAMPLE 93

(6S)-N-[(6-Amino-2-hydroxymethyl-3-pyridyl)methyl]-3-[(2,2-diphenylethyl)amino]-4-oxo-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, 2,2-diphenylethylamine and the compound described in Preparation G.

EXAMPLE 94

(3R)-N-[(6-Amino-2-methyl-3-pyridyl)methyl]-6-[(2,2-diphenylethyl)amino]-1-methyl-5-oxo-1,2,3,5-tetrahydroimidazo[1,2-a]pyrazine-3-carboxamide dihydrochloride Step A : Benzyl (4R)-1-methyl-2-oxo-4-imidazolidinecarboxylate The expected product is obtained according to the process described in Synth. Commun. 1996, 26 (11), 2165–75.

Step B: (3R)-N-[(6-Amino-2-methyl-3-pyridyl) methyl]-6-[(2,2-diphenylethyl)amino]-1-methyl-5-oxo-1,2,3,5-tetrahydroimidazo[1,2-a]pyrazine-3-carboxamide dihydrochloride The expected product is obtained according to the process described in Example 1, starting from the compound obtained in the preceding Step, 2,2-diphenylethylamine and the compound described in Preparation A.

EXAMPLE 95

(8S)-N-[(6-Amino-2-methyl-3-pyridyl)methyl]-2-oxo-3-(2-phenethylamino)-1,4-diazabicyclo[4.2.0]octa-3,5-diene-8-carboxamide dihydrochloride The expected product is obtained according to the process described in Example 1, starting from benzyl (2S)-4-oxo-2-azetidinecarboxylate, 2-phenethylamine and the compound described in Preparation A.

EXAMPLE 96

(6S)-N-[(6-Amino-2-methyl-3-pyridyl)methyl]-4-oxo-3-(2-phenethylamino)-4,6,7,8,9,10-hexahydropyrazino[1,2-a]azepine-6-carboxamide dihydrochloride The expected product is obtained according to the process described in Example 1, starting from benzyl (2S)-7-oxo-2-azepanecarboxylate, 2-phenethylamine and the compound described in Preparation A.

EXAMPLE 97

(6R)-N-[(6-Amino-2-methyl-3-pyridyl)-methyl]-3-[2,2-bis-(4-methoxyphenyl)-ethylamino]-4-oxo-4,6,7,8-tetrahydropyrrolo[1,2-a]pyrazine-6-carboxamide dihydrochloride The expected product is obtained according to the process described in Example 1, starting from benzyl (2R)-5- oxoprolinate, 2,2-bis-(4-methoxyphenyl)-ethylamine and the compound described in Preparation A.

EXAMPLE 98

N-[(6-Amino-2-methyl-3-pyridyl)-methyl]-3-[2,2-bis-(4-methoxy-phenyl)-ethylamino]-4-oxo-4,6,7,8-tetrahydropyrrolo[1,2-a]pyrazine-6-carboxamide dihydrochloride The expected product is obtained according to the process described in Example 1, starting from benzyl (±)-5-oxoprolinate, 2,2-bis-(4-methoxyphenyl)-ethylamine and the compound described in Preparation A.

Elemental Microanalysis

|  | %C | %H | %N | %Cl |
|---|---|---|---|---|
| Calculated: | 59.33 | 5.78 | 13.39 | 11.30 |
| Found: | 60.19 | 5.70 | 13.50 | 11.61 |

EXAMPLE 99

(6S)-N-[(6-Amino-2-methyl-3-pyridyl)-methyl]-4-oxo-3-[(2R)-2-(5-methyl-2-pyridyl)-2-(2,4-difluorophenyl)-ethylamino]-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, (2R)-2-(5-methyl-2-pyridyl)-2-(2,4-difluorophenyl)-ethylamine and the compound described in Preparation A.

EXAMPLE 100

(6S)-N-[(6-Amino-2-methyl-3-pyridyl)-methyl]-4-oxo-3-[(2S)-2-(5-methyl-2-pyridyl)-2-(2,4-difluorophenyl)-ethylamino]-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, (2S)-2-(5-methyl-2-pyridyl)-2-(2,4-difluorophenyl)-ethylamine and the compound described in Preparation A.

EXAMPLE 101

(6S)-N-[(6-Amino-2-methyl-3-pyridyl)-methyl]-4-oxo-3-amino-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, di-(tert-butyl)imidodicarbonate and the compound described in Preparation A.

EXAMPLE 102

(4S)-N-[(6-Amino-2-methyl-3-pyridyl)-methyl]-1-methyl-6-oxo-7-(2-phenethylamino)-1,3,4,6-tetrahydro-2H-pyrazino[1,2-a]pyrimidine-4-carboxamide dihydrochloride The expected product is obtained according to the process described in Example 1, starting from benzyl (4S)-1-methyl-2-oxo-hexahydro-4-pyrimidinecarboxylate, 2-phenethylamine and the compound described in Preparation A.

EXAMPLE 103

(6S)-N-[(2-Ethylcarbamoylmethoxy)-benzyl]-4-oxo-3-(2,2-diphenylethylamino)-4,6,7,8-tetrahydropyrrolo[1,2-a]pyrazine-6-carboxamide hydrochloride The expected product is obtained according to the process described in Steps F to I of Example 1, starting from the compound described in Step E of Example 1, 2-diphenylethylamine and the compound described in Preparation E.

Elemental Microanalysis

|  | %C | %H | %N | %Cl |
|---|---|---|---|---|
| Calculated: | 65.83 | 6.03 | 11.63 | 5.89 |
| Found: | 65.82 | 6.00 | 11.57 | 5.64 |

EXAMPLE 104

(6S)-N-[(6-Amino-2-methyl-3-pyridyl)-methyl]-4-oxo-3-[(2-phenylcyclopropyl)amino]-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, (2-phenylcyclopropyl)amine and the compound described in Preparation A.

EXAMPLE 105

(6S)-N-[(6-Amino-2-methyl-3-pyridyl)-methyl]-4-oxo-3-[(2,2-diphenyl-cyclopropyl)amino]-4,6,7,8-tetrahydropyrrolo[1,2-a]pyrazine-6-carboxamide dihydrochloride The expected product is obtained according to the process described in Steps F to I of Example 1, starting from the compound described in Step E of Example 1, (2,2-diphenylcyclopropyl)amine and the compound described in Preparation A.

EXAMPLE 106

(6S)-N-[(6-Amino-2-methyl-3-pyridyl)-methyl]-4-oxo-3-[(2R)-2-(2,4-dimethylphenyl)-2-(5-ethyl-2-pyrimidinyl)ethylamino]-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, (2R)-2-(2,4-dimethylphenyl)-2-(5-ethyl-2-pyrimidinyl)ethylamine and the compound described in Preparation A.

EXAMPLE 107

(6S)-N-[(6-Amino-2-methyl-3-pyridyl)-methyl]-4-oxo-3-[(2S)-2-(2,4-dimethylphenyl)-2-(5-ethyl-2-pyrimidinyl)ethylamino]-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, (2S)-2-(2,4-dimethylphenyl)-2-(5-ethyl-2-pyrimidinyl)ethylamine and the compound described in Preparation A.

EXAMPLE 108

(6S)-N-[(6-Amino-2-methyl-3-pyridyl)-methyl]-4-oxo-3-[(2R)-2-(5-methyl-2-pyridyl)-2-(p-tolyl)-ethylamino]-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, (2R)-2-(5-methyl-2-pyridyl)-2-(p-tolyl)-ethylamine and the compound described in Preparation A.

EXAMPLE 109

(6S)-N-[(6-Amino-2-methyl-3-pyridyl)-methyl]-4-oxo-3-[(2S)-2-(5-methyl-2-pyridyl)-2-(p-tolyl)-ethylamino]-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, (2S)-2-(5-methyl-2-pyridyl)-2-(p-tolyl)-ethylamine and the compound described in Preparation A.

EXAMPLE 110

(6S)-N-[(6-Amino-2-methyl-3-pyridyl)-methyl]-4-oxo-3-[(2R)-2-(5-methoxy-2-pyridyl)-2-(4-methoxyphenyl)-ethylamino]-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, (2R)-2-(5-methoxy-2-pyridyl)-2-(4-methoxyphenyl)-ethylamine and the compound described in Preparation A.

EXAMPLE 111

(6S)-N-[(6-Amino-2-methyl-3-pyridyl)-methyl]-4-oxo-3-[(2S)-2-(5-methoxy-2-pyridyl)-2-(4-methoxyphenyl)-ethylamino]-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, (2S)-2-(5-methoxy-2-pyridyl)-2-(4-methoxyphenyl)-ethylamine and the compound described in Preparation A.

EXAMPLE 112

(6S)-N-[(6-Amino-2-methyl-3-pyridyl)-methyl]-4-oxo-3-[(2R)-2-(5-methoxy-2-pyridyl)-2-(3,4-dimethylphenyl)-ethylamino]-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, (2R)-2-(5-methoxy-2-pyridyl)-2-(3,4-dimethylphenyl)-ethylamine and the compound described in Preparation A.

EXAMPLE 113

(6S)-N-[(6-Amino-2-methyl-3-pyridyl)-methyl]-4-oxo-3-[(2S)-2-(5-methoxy-2-pyridyl)-2-(3,4-dimethylphenyl)-ethylamino]-4,6,7,8-tetrahydropyrrolo[1,2-a]pyrazine-6-carboxamide trihydrochloride The expected product is obtained according to the process described in Steps F to I of Example 1, starting from the compound described in Step E of Example 1, (2S)-2-(5-methoxy-2-pyridyl)-2-(3,4-dimethylphenyl)-ethylamine and the compound described in Preparation A.

Following examples are prepared according to the process described in example 1 using the corresponding starting materials.

EXAMPLE 114

N-[(6-Amino-2-methyl-3-pyridyl)-methyl]-3-[(2,2-diphenyl-ethyl)amino]-4-oxo-4,6,7,8-tetrahydropyrrolo]1,2-a]pyrazine-6-carboxamide dihydrochloride Elemental Microanalysis

| | %C | %H | %N | %C |
|---|---|---|---|---|
| Calculated: | 61.38 | 5.68 | 14.81 | 12.49 |
| Found: | 61.97 | 5.76 | 15.10 | 12.41 |

EXAMPLE 115

(6R)-N-[(6-Amino-2-methyl-3-pyridyl)-methyl]-3-[(2,2-diphenylethyl)amino]-4-oxo-4,6,7,8-tetrahydropyrrolo[1,2-a]pyrazine-6-carboxamide dihydrochloride

EXAMPLE 116

(6S)-N-[(6-Amino-2-methyl-3-pyridyl)-methyl]-4-oxo-3-[(2R)-2-(2-pyridyl)-2-(4-trifluoromethoxyphenyl)-ethylamino]-4,6,7,8-tetrahydropyrrolo[1,2-a]pyrazine-6-carboxamide trihydrochloride

EXAMPLE 117

(6S)-N-[(6-Amino-2-methyl-3-pyridyl)-methyl]-4-oxo-3-[(2S)-2-(2-pyridyl)-2-(4-trifluoromethoxyphenyl)-ethylamino]-4,6,7,8-tetrahydropyrrolo[1,2-a]pyrazine-6-carboxamide trihydrochloride

EXAMPLE 118

(6S)-N-[(6-Amino-2-methyl-3-pyridyl)-methyl]-4-oxo-3-[(2R)-2-(4,6-dimethyl-2-pyridyl)-2-(4-methoxyphenyl)-ethylamino]-4,6,7,8-tetrahydropyrrolo[1,2-a]pyrazine-6-carboxamide trihydrochloride

EXAMPLE 119

(6S)-N-[(6-Amino-2-methyl-3-pyridyl)-methyl]-4-oxo-3-[(2S)-2-(4,6-dimethyl-2-pyridyl)-2-(4-methoxyphenyl)-ethylamino]-4,6,7,8-tetrahydropyrrolo[1,2-a]pyrazine-6-carboxamide trihydrochloride

EXAMPLE 120

(6S)-N-[(6-Amino-2-methyl-3-pyridyl)-methyl]-4-oxo-3-[(2R)-2-(5-methyl-2-pyridyl)-2-(2-fluoro-4-methoxyphenyl)-ethylamino]-4,6,7,8-tetrahydropyrrolo[1,2-a]pyrazine-6-carboxamide trihydrochloride

EXAMPLE 121

(6S)-N-[(6-Amino-2-methyl-3-pyridyl)-methyl]-4-oxo-3-[(2S)-2-(5-methyl-2-pyridyl)-2-(2-fluoro-4-methoxyphenyl)-ethylamino]-4,6,7,8-tetrahydropyrrolo[1,2-a]pyrazine-6-carboxamide trihydrochloride

EXAMPLE 122

(6S)-N-[(6-Amino-2-methyl-3-pyridyl)-methyl]-4-oxo-3-[(2R)-2-(5-methoxy-2-pyridyl)-2-(2,6-dimethyl-4-methoxyphenyl)-ethylamino]-4,6,7,8-tetrahydropyrrolo[1,2-a]pyrazine-6-carboxamide trihydrochloride

EXAMPLE 123

(6S)-N-[(6-Amino-2-methyl-3-pyridyl)-methyl]-4-oxo-3-[(2S)-2-(5-methoxy-2-pyridyl)-2-(2,6-dimethyl-4-methoxyphenyl)-ethylamino]-4,6,7,8-tetrahydropyrrolo[1,2-a]pyrazine-6-carboxamide trihydrochloride

EXAMPLE 124

(6S)-N-[(6-Amino-2-methyl-3-pyridyl)-methyl]-4-oxo-3-[(2R)-2-(4,6-dimethyl-2-pyridyl)-2-(4-methyl-2-methoxyphenyl)-ethylamino]-4,6,7,8-tetrahydropyrrolo[1,2-a]pyrazine-6-carboxamide trihydrochloride

EXAMPLE 125

(6S)-N-[(6-Amino-2-methyl-3-pyridyl)-methyl]-4-oxo-3-[(2S)-2-(4,6-dimethyl-2-pyridyl)-2-(4-methyl-2-methoxyphenyl)-ethylamino]-4,6,7,8-tetrahydropyrrolo[1,2-a]pyrazine-6-carboxamide trihydrochloride

EXAMPLE 126

(6S)-N-[(6-Amino-2-methyl-3-pyridyl)-methyl]-3-[2,2-bis-(4-dimethylamino-phenyl)-ethylamino]-4-oxo-4,6,7,8-ttrahydropyrrolo[1,2-a]pyrazine-6-carboxamide tetrahydrochloride

EXAMPLE 127

(6S)-N-[(6-Amino-2-methyl-3-pyridyl)-methyl]-3-[2,2-bis-(2-fluorophenyl)-ethylamino]-4-oxo-4,6,7,8-tetrahydropyrrolo[1,2-a]pyrazine-6-carboxamide dihydrochloride

EXAMPLE 128

(6S)-N-[(6-Amino-2-methyl-3-pyridyl)-methyl]-3-[2,2-bis-(2-methoxy-phenyl)-ethylamino]-4-oxo-4,6,7,8-tetrahydropyrrolo[1,2-a]pyrazine-6-carboxamide dihydrochloride

EXAMPLE 129

(6S)-N-[(6-Amino-2-methyl-3-pyridyl)-methyl]-3-[2,2-bis-(2-chlorophenyl)-ethylamino]-4-oxo-4,6,7,8-tetrahydropyrrolo[1,2-a]pyrazine-6-carboxamide dihydrochloride

EXAMPLE 130

(6S)-N-[(6-Amino-2-methyl-3-pyridyl)-methyl]-3-[2,2-bis-(2-hydroxy-phenyl)-ethylamino]-4-oxo-4,6,7,8-tetrahydropyrrolo[1,2-a]pyrazine-6-carboxamide dihydrochloride

EXAMPLE 131

(6S)-N-[(6-Amino-2-methyl-3-pyridyl)-methyl]-3-[2,2-bis-(3-methoxy-phenyl)-ethylamino]-4-oxo-4,6,7,8-tetrahydropyrrolo[1,2-a]pyrazine-6-carboxamide dihydrochloride

EXAMPLE 132

(6S)-N-[(6-Amino-2-methyl-3-pyridyl)-methyl]-3-[2,2-bis-(3-fluorophenyl)-ethylamino]-4-oxo-4,6,7,8-tetrahydropyrrolo[1,2-a]pyrazine-6-carboxamide dihydrochloride

EXAMPLE 133

(6S)-N-[(6-Amino-2-methyl-3-pyridyl)-methyl]-3-[2,2-bis-(3-chlorophenyl)-ethylamino]-4-oxo-4,6,7,8-tetrahydropyrrolo[1,2-a]pyrazine-6-carboxamide dihydrochloride

EXAMPLE 134

(6S)-N-[(6-Amino-2-methyl-3-pyridyl)-methyl]-3-[2,2-bis-(3-hydroxy-phenyl)-ethylamino]-4-oxo-4,6,7,8-tetrahydropyrrolo[1,2-a]pyrazine-6-carboxamide dihydrochloride

EXAMPLE 135

(6S)-N-[(6-Amino-2-methyl-3-pyridyl)-methyl]-4-oxo-3-[(2R)-2-(4-methoxy-phenyl)-2-(2-benzo[c]pyridyl)-ethylamino]-4,6,7,8-tetrahydropyrrolo[1,2-a]pyrazine-6-carboxamide trihydrochloride

EXAMPLE 136

(6S)-N-[(6-Amino-2-methyl-3-pyridyl)-methyl]-4-oxo-3-[(2S)-2-(4-methoxy-phenyl)-2-(2-benzo[c]pyridyl)-ethylamino]-4,6,7,8-tetrahydropyrrolo[1,2-a]pyrazine-6-carboxamide trihydrochloride

EXAMPLE 137

(6S)-N-[(6-Amino-2-methyl-3-pyridyl)-methyl]-3-[2,2-bis-(2-thienyl)-ethylamino]-4-oxo-4,6,7,8-tetrahydropyrrolo[1,2-a]pyrazine-6-carboxamide dihydrochloride

EXAMPLE 138

(6S)-N-[(6-Amino-2-methyl-3-pyridyl)-methyl]-4-oxo-3-[(2R)-2-phenyl-2-phenethylamino]-4,6,7,8-tetrahydropyrrolo[1,2-a]pyrazine-6-carboxamide, carboxamide dihydrochloride

EXAMPLE 139

(6S)-N-[(6-Amino-2-methyl-3-pyridyl)-methyl]-4-oxo-3-[(2S)-2-phenyl-2-phenethylamino]-4,6,7,8-tetrahydropyrrolo[1,2-a]pyrazine-6-carboxamide, carboxamide dihydrochloride

EXAMPLE 140

(6S)-N-[(6-Amino-2-methyl-3-pyridyl)-methyl]-4-oxo-3-[(2R)-2-hydroxy-2-phenyl-2-phenethylamino]-4,6,7,8-tetrahydropyrrolo[1,2-a]pyrazine-6-carboxamide, carboxamide dihydrochloride

EXAMPLE 141

(6S)-N-[(6-Amino-2-methyl-3-pyridyl)-methyl]-4-oxo-3-[(2S)-2-hydroxy-2-phenyl-2-phenethylamino]-4,6,7,8-tetrahydropyrrolo[1,2-a]pyrazine-6-carboxamide, carboxamide dihydrochloride

EXAMPLE 142

(6S)-N-[(6-Amino-2-methyl-3-pyridyl)-methyl]-4-oxo-3-[N-methyl-2-phenyl-2-phenethylamino]-4,6,7,8-tetrahydropyrrolo[1,2-a]pyrazine-6-carboxamide dihydrochloride

EXAMPLE 143

(6S)-N-[(6-Amino-2-methyl-3-pyridyl)-methyl]-4-oxo-3-[N-methyl-2-(2-pyridyl)-2-phenethylamino]-4,6,7,8-tetrahydropyrrolo[1,2-a]pyrazine-6-carboxamide trihydrochloride

EXAMPLE 144

(6S)-N-[(6-Amino-2-methyl-3-pyridyloxyde)-methyl]-3-[(2,2-diphenylethyl)amino]-4-oxo-4,6,7,8-tetrahydropyrrolo[1,2-a]pyrazine-6-carboxamide dihydrochloride

EXAMPLE 145

(6S)-N-[(4,6-Dimethyl-2-ethylaminocarbonylmethoxy-3-pyridyl)-methyl]-3-[(2,2-diphenylethyl)amino]-4-oxo-4,6,7,8-tetrahydropyrrolo[1,2-a]pyrazine-6-carboxamide dihydrochloride

EXAMPLE 146

(6S)-N-[(2-Ethylcarbamoylmethoxy)-benzyl]-4-oxo-3-[(2R)-2-(5-methyl-2-pyridyl)-2-(p-tolyl)ethylamino]-4,6,7,8-tetrahydropyrrolo[1,2-a]pyrazine-6-carboxamide dihydrochloride

EXAMPLE 147

(6S)-N-[(2-Ethylcarbamoylmethoxy)-benzyl]-4-oxo-3-[(2S)-2-(5-methyl-2-pyridyl)-2-(p-tolyl)ethylamino]-4,6,7,8-tetrahydropyrrolo[1,2-a]pyrazine-6-carboxamide dihydrochloride

EXAMPLE 148

(6S)-N-[(6-Amino-2,5-dimethyl-3-pyridyl)-methyl]-3-[(2R)-2-(5-methyl-2-pyridyl)-2-(p-tolyl)-ethylamino]-4-oxo-4,6,7,8-tetrahydropyrrolo[1,2-a]pyrazine-6-carboxamide trihydrochloride

EXAMPLE 149

(6S)-N-[(6-Amino-2,5-dimethyl-3-pyridyl)-methyl]-3-[(2S)-2-(5-methyl-2-pyridyl)-2-(p-tolyl)-ethylamino]-4-oxo-4,6,7,8-tetrahydropyrrolo[1,2-a]pyrazine-6-carboxamide trihydrochloride

EXAMPLE 150

(6S)-N-[(6-Amino-2-methyl-3-pyridyl)-methyl]-4-oxo-3-[(2R)-2-(5-methyl-2-pyridyl)-2-(4-methyl-2-methoxyphenyl)-ethylamino-]-4,6,7,8-tetrahydropyrrolo[1,2-a]pyrazine-6-carboxamide trihydrochloride

EXAMPLE 151

(6S)-N-[(6-Amino-2-methyl-3-pyridyl)-methyl]-4-oxo-3-[(2S)-2-(5-methyl-2-pyridyl)-2-(4-methyl-2-methoxyphenyl)-ethylamino]-4,6,7,8-tetrahydropyrrolo[1,2-a]pyrazine-6-carboxamide trihydrochloride

EXAMPLE 152

(6S)-N-[(6-Amino-2-methyl-3-pyridyl)-methyl]-4-oxo-3-[(2R)-2-(4,6-dimethyl-2-pyridyl)-2-(2,4-dimethoxyphenyl)-ethylamino]-4,6,7,8-tetrahydropyrrolo[1,2-a]pyrazine-6-carboxamide trihydrochloride

EXAMPLE 153

(6S)-N-[(6-Amino-2-methyl-3-pyridyl)-methyl]-4-oxo-3-[(2S)-2-(4,6-dimethyl-2-pyridyl)-2-(2,4-dimethoxyphenyl)-ethylamino]-4,6,7,8-tetrahydropyrrolo[1,2-a]pyrazine-6-carboxamide trihydrochloride Pharmacological Study of the Compounds of the Invention

EXAMPLE 154

Anti-coagulant Activity, Measurement of Thrombin Time and Activated Cephalin Time in Humans In order to evaluate the anti-coagulant activity of the compounds of the invention, the thrombin time (TT) and activated cephalin time (ACT) were determined from human plasma samples. An $ST_4$ coagulometer (Diagnostica Stago, France) was used. Plasma, deficient in platelets and lyophilised (Stago), is taken up in distilled water. The TT is obtained using the reagent Prest Thrombin and the ACT using the reagent PTT Automate Cephalin.

Inhibitor or solvent (10 $\mu$l) is added to the plasma (90 $\mu$l), and incubation is carried out for 2 minutes at 37° C. 100 $\mu$l of Prest Thrombin (TT) or PTT Automate Cephalin (ACT) are added and at the same time the stopwatch is started.

Under those conditions, the TT is of the order of 18 seconds and the ACT is of the order of 12 seconds. The activity of an antagonist is evaluated by its capacity to prolong the TT and the ACT relative to the control. The effect of the inhibitors is expressed by the concentration in $\mu$M that doubles the coagulation time ($Ctt_2$).

The compounds of the invention caused very significant prolongation of the coagulation times and the $Ctt_2$ are given in Table 1 below by way of example:

TABLE 1

| Example | TT $Ctt_2$ ($\mu$M) | ACT $Ctt_2$ ($\mu$M) |
|---|---|---|
| 1 | 3 | 9.1 |
| 6 | 0.4 | 2.5 |
| 7 | 3 | 9.1 |
| 15 | 0.11 | 1.3 |

TABLE 1-continued

| Example | TT $Ctt_2$ ($\mu$M) | ACT $Ctt_2$ ($\mu$M) |
|---|---|---|
| 16 | 0.17 | 1.6 |
| 20 | 0.15 | 2.17 |
| 22 | 0.22 | 3.07 |
| 23 | 0.24 | 2.75 |
| 68 | 0.23 | 2.04 |
| 98 | 0.33 | 3.54 |
| 103 | 0.96 | 3.65 |

EXAMPLE 155

Inhibition of Thrombin and of Fibrinolysis Serine Proteases

For in vitro evaluation of the inhibitory activity of the products of the invention on human thrombin (Sigma, specific activity 3230 UNIH/mg), purified human fibrinogen (4 mM, Stago) (Fg) was added to a given amount of thrombin (0.7 nM) that had previously been incubated with or without the inhibitor to be tested (20° C., 10 minutes).

For in vitro evaluation of the selectivity of the products in respect of plasmin, the same protocol was applied to purified human plasmin (2 nM, Stago), using as substrate a paranitroanilide-containing peptide: <Glu-Phe-Lys-pNA (0.50 mM, S 2403, Kabi).

Inhibitors, enzymes and substrates are diluted in the same buffer (0.01 mM phosphate buffer, pH 7.4, containing 0.12 M sodium chloride and 0.05% of bovine serum albumin) and then distributed on a polystyrene microtitre plate in a volume of 50 $\mu$l.

The fibrin formed by the thrombin or by the paranitroanilide released by the action of the serine protease is measured using a spectrophotometer at 405 nm after from 15 to 30 minutes' reaction at 20° C.

Table 2 below gives in nM the concentration of the compounds that inhibits 50% of the enzymatic activity ($IC_{50}$) of the thrombin compared with the control without product. The results obtained show that the compounds of the invention are potent inhibitors of human thrombin in respect of human fibrinogen.

TABLE 2

| Example | $IC_{50}$ (nM) |
|---|---|
| 1 | 34 |
| 6 | 11 |
| 7 | 42 |
| 15 | 7 |
| 16 | 17 |
| 20 | 6 |
| 22 | 20 |
| 23 | 3.9 |
| 40 | 43 |
| 50 | 29 |
| 68 | 16 |
| 71 | 13 |
| 98 | 8 |
| 103 | 14 |

Table 3 below gives in nM the concentration of the compounds that inhibits 50% of the enzymatic activity ($IC_{50}$) of the fibrinolysis proteases. The results obtained show that the compounds of the invention have very significant selectivity towards fibrinolysis serine proteases.

TABLE 3

| Example | IC$_{50}$ (nM) | | |
|---|---|---|---|
| | Plasmin | t-PA | uPA |
| 1 | >33000 | >33000 | >33000 |
| 6 | >33000 | >33000 | >33000 |
| 7 | >33000 | >33000 | >33000 |
| 15 | >33000 | >33000 | >33000 |
| 71 | >33000 | >33000 | >33000 |
| 98 | >33000 | >33000 | >33000 |

EXAMPLE 156

Anti-coagulant Activity After Administration per os to Dogs

Male or female dogs weighing from 11 to 28 kg are treated orally with the products of the invention (5 or 10 mg/kg). The coagulation times (TT, ACT) are determined from dog plasma samples 10 minutes before and 30 min, 1 hour, 2 hours, 4 hours and 6 hours after administration of the products. The measurements of the coagulation times are carried out as described in Example 114.

Under the conditions of our experiments, the TT is of the order of 19 seconds and the ACT is of the order of 18 seconds.

The substances of the invention significantly increase the TT and ACT in the animals. Table 4 summarises the results obtained.

The results show the maximum increase in the TT and ACT obtained after p.o. treatment of the dogs. The values demonstrate the number of times by which the initial time has been

TABLE 4

Maximum TT and ACT increase
(number of times by which the initial time has been increased)

| Example | Dose (mg/kg) | TT | ACT |
|---|---|---|---|
| 1 | 3 | 3.6 | 1.6 |
| 6 | 10 | 6.2 | 1.7 |
| 7 | 3 | 2.5 | 1.4 |
| 15 | 3 | 7 | 1.6 |
| 16 | 10 | 13.3 | 2.4 |
| 20 | 3 | 4.4 | 1.4 |
| 22 | 10 | 4.5 | 1.5 |
| 98 | 10 | 6.1 | 1.4 |

EXAMPLE 157

Formulation for the preparation of 1000 tablets each containing a dose of 10 mg:

Pharmaceutical Composition

| Compound of Example 1 | 10 g |
|---|---|
| Hydroxypropyl cellulose | 2 g |
| Wheat starch | 10 g |
| Lactose | 100 g |
| Magnesium stearate | 3 g |
| Talc | 3 g |

What is claimed is:
1. A compound selected from those of formula (I):

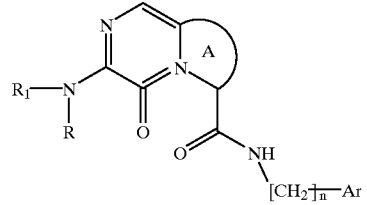

(I)

wherein:
R$_1$ represents hydrogen or linear or branched (C$_1$–C$_6$) alkyl which is optionally substituted by one or more identical or different substituents selected from aryl, heteroaryl, cycloalkyl, heterocycloalkyl, carboxy, linear or branched (C$_1$–C$_6$)-alkoxycarbonyl, carbamoyl and hydroxy, cycloalkyl, heterocycloalkyl, or a group of formula (G):

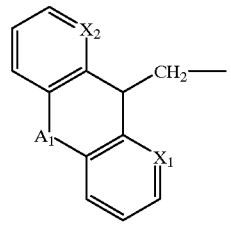

(G)

wherein A$_1$ represents a single bond, —CH$_2$—, —CH$_2$—CH$_2$—, or —N(CH$_3$)—, or oxygen, or sulphur, and X$_1$ and X$_2$, which may be identical or different, each represents carbon or nitrogen, R represents hydrogen or linear or branched (C$_1$–C$_6$) alkyl,

represents a saturated ring having 4 to 7 ring members that may contain in addition to nitrogen one or two hetero atoms selected from O and S, or —N(R$_2$), R$_2$ represents hydrogen or linear or branched (C$_1$–C$_6$) alkyl, n represents an integer wherein 1≦n≦6, Ar represents aryl or heteroaryl, its isomers, N-oxydes and pharmaceutically-acceptable acid or base addition salts thereof, wherein:

"aryl" is understood to mean phenyl, biphenylyl or naphthyl, each of those groups being optionally substituted by one or more halogen and/or by one or more identical or different groups selected from linear or branched (C$_1$–C$_6$)alkyl which is optionally substituted by hydroxy or carboxy or by carbamoyl which is itself optionally substituted by one or two linear or branched ($C_1$–$C_6$)alkyl, or by linear or branched ($C_1$–$C_6$)alkoxy, hydroxy, trihalo-($C_1$–$C_6$)alkyl in which alkyl is linear or branched, trihalogenoalkoxy in which alkyl is linear or branched, amino which is optionally substituted by one or two linear or branched ($C_1$–$C_6$)alkyl, or by linear or branched alkylcarbonyloxy, carboxymethoxy and carbamoylmethoxy which is N-substituted by one or two linear or branched ($C_1$–$C_6$)alkyl, "heteroaryl" is understood to a mean mono- or bi-cyclic aromatic group having 5 to 12 ring members and containing one, two or three hetero atoms selected from oxygen, nitrogen and sulphur, it being understood that the heteroaryl may be optionally substituted by one or more halogen atoms and/or by one or more identical or different groups selected from linear or branched ($C_1$–$C_6$)alkyl which is optionally substituted by hydroxy or carboxy or by carbamoyl which is itself optionally substituted by one or two linear or branched ($C_1$–$C_6$)alkyl, or by hydroxy, linear or branched ($C_1$–$C_6$)alkoxy, trihalo-($C_1$–$C_6$)alkyl in which alkyl is linear or branched, phenyl, amino which is optionally N-substituted by one or more linear or branched ($C_1$–$C_6$)alkyl, or by carboxymethoxy or carbamoylmethoxy which is optionally substituted by one or two linear or branched ($C_1$–$C_6$)alkyl, "cycloalkyl" is understood to mean a saturated or unsaturated mono-cyclic or bi-cyclic hydrocarbon having 3 to 12 ring members, it being understood that the ring system may be optionally substituted by one or more halogen and/or by one or more identical or different groups selected from linear or branched ($C_1$–$C_6$)alkyl, linear or branched ($C_1$–$C_6$)alkoxy, hydroxy, trihalo-($C_1$–$C_6$)alkyl in which alkyl is linear or branched, amino which is optionally substituted by one or more linear or branched ($C_1$–$C_6$)alkyl and aryl, and "heterocycloalkyl" being understood to mean a saturated or unsaturated mono-cyclic or bi-cyclic ring system having 4 to 12 ring members and containing one, two or three hetero atoms selected from oxygen, nitrogen and sulphur, it being understood that the heterocycle may be optionally substituted by one or more halogen atoms and/or by one or more identical or different groups selected from linear or branched ($C_1$–$C_6$)alkyl, linear or branched ($C_1$–$C_6$)alkoxy, hydroxy, trihalo-($C_1$–$C_6$)alkyl in which alkyl is linear or branched, amino which is optionally substituted by one or more linear or branched ($C_1$–$C_6$)alkyl groups, aryl and diarylmethyl.

2. A compound of claim 1 wherein n is 1.

3. A compound of claim 1 wherein

represents pyrrolidinyl.

4. A compound of claim 1 wherein Ar represents phenyl or pyridyl, each of those groups being optionally substituted by one or more halogen atoms and/or by one or more identical or different groups selected from linear or branched ($C_1$–$C_6$)alkyl which is optionally substituted by hydroxy or carboxy or by carbamoyl which is itself optionally substituted by one or two linear or branched ($C_1$–$C_6$)alkyl, linear or branched ($C_1$–$C_6$)alkoxy, hydroxy, trihalo-($C_1$–$C_6$)alkyl in which alkyl is linear or branched, amino which is optionally substituted by one or two linear or branched ($C_1$–$C_6$) alkyl), carboxymethoxy and carbamoylmethoxy which is optionally N-substituted by one or two linear or branched ($C_1$–$C_6$)alkyl.

5. A compound of claim 4 wherein Ar represents pyridyl optionally substituted by one or more halogen and/or by one or more identical or different groups selected from linear or branched ($C_1$–$C_6$)alkyl which is optionally substituted by hydroxy or carboxy or by carbamoyl which is itself optionally substituted by one or two linear or branched ($C_1$–$C_6$) alkyl, linear or branched ($C_1$–$C_6$)alkoxy, hydroxy, trihalo-($C_1$–$C_6$)alkyl in which alkyl is linear or branched, amino which is optionally substituted by one or two linear or branched ($C_1$–$C_6$)alkyl, carboxymethoxy and carbamoylmethoxy which is optionally N-substituted by one or two linear or branched ($C_1$–$C_6$)alkyl.

6. A compound of claim 1 which is selected from (6S)-N-[(6-amino-2-methyl-3-pyridyl)methyl]-4-oxo-3-(2-phenethylamino)-4,6,7,8-tetrahydropyrrolo[1,2-a]-pyrazine-6-carboxamide, its isomers, N-oxydes, and pharmaceutically-acceptable acid or base addition salts thereof.

7. A method-of-treating a living animal body afflicted with a condition requiring an anticoagulant comprising the step of administering to the living animal body an amount of a compound of claim 1 which is effective for alleviation of said condition.

8. A pharmaceutical composition containing as active ingredient an effective anticoagulant amount of a compound of claim 1, together with one or more pharmaceutically-acceptable excipients or vehicles.

* * * * *

UNITED STATES PATENT AND TRADEMARK OFFICE
CERTIFICATE OF CORRECTION

PATENT NO.   : 6,277,851 B1
DATED        : August 21, 2001
INVENTOR(S)  : Guillaume De Nanteuil et al.

It is certified that error appears in the above-identified patent and that said Letters Patent is hereby corrected as shown below:

Title page,
ABSTRACT, Formula (I) please remove the double bond from drawing as per originally submitted drawing.

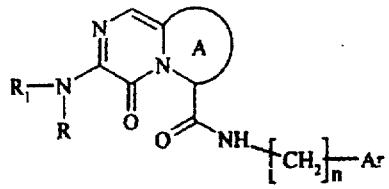

Column 42,
Line 10, please remove the double bond from drawing as per originally submitted drawing.

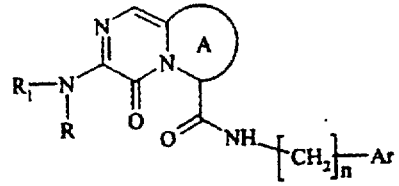

Column 43,
Line 9, please add -- optionally -- before "N-substituted"
Line 11, please add -- a -- before "mono-".

Signed and Sealed this

Fifth Day of March, 2002

JAMES E. ROGAN
Director of the United States Patent and Trademark Office